(12) United States Patent
Van Orsdol

(10) Patent No.: US 9,360,467 B1
(45) Date of Patent: Jun. 7, 2016

(54) APPARATUS AND METHOD FOR A DUAL CHAMBER COPPER STRIP CORROSION TEST OF HIGH VAPOR PRESSURE PRODUCTS

(71) Applicant: Fred G. Van Orsdol, Owasso, OK (US)

(72) Inventor: Fred G. Van Orsdol, Owasso, OK (US)

( * ) Notice: Subject to any disclaimer, the term of this patent is extended or adjusted under 35 U.S.C. 154(b) by 0 days.

(21) Appl. No.: 14/966,404

(22) Filed: Dec. 11, 2015

Related U.S. Application Data

(60) Provisional application No. 62/091,863, filed on Dec. 15, 2014.

(51) Int. Cl.
*G01N 33/22* (2006.01)
*G01N 33/00* (2006.01)
*G01N 17/04* (2006.01)

(52) U.S. Cl.
CPC .......... *G01N 33/225* (2013.01); *G01N 33/0009* (2013.01); *G01N 17/04* (2013.01)

(58) Field of Classification Search
CPC ..... G01N 33/225; G01N 33/22; G01N 33/00; G01N 33/0009; G01N 33/0004; G01N 17/04; G01N 17/00
USPC ........................... 436/6, 2; 422/53, 50
See application file for complete search history.

(56) References Cited

U.S. PATENT DOCUMENTS

| | | | |
|---|---|---|---|
| 3,259,466 | A | 7/1966 | Jacks, Jr. |
| 3,504,323 | A | 3/1970 | Meany, Jr. |
| 5,332,900 | A | 7/1994 | Witzke et al. |
| 6,454,922 | B1 | 9/2002 | Weisbrod |
| 8,033,164 | B2 | 10/2011 | Dermody et al. |
| 8,513,020 | B2 | 8/2013 | Hehn et al. |
| 8,951,802 | B2 | 2/2015 | Bridenbaker |

OTHER PUBLICATIONS kohlerinstrument.com, Fuels, Kohler Instruement, May 11, 2013, pp. 79-180.*

* cited by examiner

*Primary Examiner* — Christine T Mui
(74) *Attorney, Agent, or Firm* — GableGotwals

(57) ABSTRACT

An apparatus and method for copper strip corrosion testing of high vapor pressure hydrocarbon products using a dual test chamber system to provide over pressure protection to the chambers and containment of the liquid and vapor being tested.

13 Claims, 1 Drawing Sheet

APPARATUS AND METHOD FOR A DUAL CHAMBER COPPER STRIP CORROSION TEST OF HIGH VAPOR PRESSURE PRODUCTS

1. FIELD OF THE INVENTION

The present invention relates generally to the testing of high vapor pressure fluid products for corrosive contaminates. More particularly, the present invention relates to the testing for corrosive contaminates in Liquefied Petroleum Gases (LPG), propane, natural gasoline, condensates, raw natural gas condensates and other high vapor pressure hydrocarbon products.

2. BACKGROUND OF THE INVENTION

High vapor pressure hydrocarbon products are currently tested for corrosive contaminates using ASTM D-1838—Standard Test Method for Copper Strip Corrosion by LPG or other high vapor pressure hydrocarbon products. See FIG. 2. This involves using a specified test cylinder with a single cavity cylinder provided with a dip tube for venting some liquid from the cylinder (to prevent excessive pressure in the cylinder whenever the liquid-filled cylinder is warmed up) and a hook for hanging a copper strip in the remaining sample of the liquid LPG product or other high vapor pressure hydrocarbon products.

The procedure for collecting the sample and conducting the test are carefully defined in the standard, but once the sample has been caught and a portion of the liquid has been vented to the atmosphere using the dip tube, the test basically requires the cylinder containing the remaining liquid sample and the copper strip to remain in a water bath at 100 degrees Fahrenheit for one hour. The copper strip is highly polished before being inserted into the cylinder and should remain immersed in the liquid product during the test period.

Following the test period, the cylinder is de-pressured, then opened, so that the copper strip can be removed and examined. The strip is graded, depending on the degree and type of discoloration, by comparing the discoloration to a comparator chart, also specified by ASTM. Number 1 copper strips are generally considered acceptable in the industry (non-corrosive), but strips graded to be number 2 or higher are generally considered to be corrosive and off-spec.

The prior art system and method for testing has the unacceptable feature of hydrocarbons being released to the atmosphere immediately after the liquid sample is collected in the cylinder. The purpose of the venting is to provide some outage and prevent over-pressuring a liquid-filled cylinder if the ambient temperature is warmer than the cylinder containing the sample or when the cylinder is immersed in the 100 degree Fahrenheit water bath called for by the test procedure. This is particularly dangerous if there are nearby ignition sources, but constitutes an environmental issue as well. It is also unsafe if the hydrocarbons are contaminated with hydrogen sulfide or other poisonous gases.

ASTM Standard D1267-12 specifies a dual chamber test apparatus. However, this is a test for vapor pressure and is not usable with the test strips needed for corrosion testing.

What is needed is a test apparatus and method that prevents the venting of volatile samples into the atmosphere near the point where the sample was collected, especially if the discharge is into the ambient air, near an ignition source, or near personnel (such as in refinery, terminal, pipeline installation or natural gas processing plant operating areas where the samples are usually collected).

Further, what is needed is a test apparatus and method that provides for the safe expansion of the hydrocarbon sample in the event the test cylinder containing the sample is warmed up by the sun or the ambient temperature after the sample is collected, or when the sample is intentionally heated in the 100 degree Fahrenheit water bath required by the copper strip corrosion test method itself.

BRIEF DESCRIPTION OF THE INVENTION

The present invention is an apparatus and method for copper strip corrosion testing of high vapor pressure hydrocarbon products using a dual chamber test apparatus. The test apparatus is provided with a second test chamber in fluid communication with the first chamber containing the test strip. An isolation valve is located between the first and second chamber and allows for isolating the first chamber while pulling a sample. The isolation valve is then opened to allow for expansion of the sample into the second chamber during the testing. The additional volume thus provided allows room for thermal expansion should the sample apparatus be warmed during the testing process, as is the usual case. The second chamber may also be equipped with a pressure gauge and/or a purge valve. The entire apparatus must be fully designed to handle the operating conditions and fluids to be encountered during its intended use.

The present invention will prevent over pressuring of the test apparatus and does not require venting sample to the atmosphere near the point of sampling, which is a routine practice with the current sampling method in ASTM D-1838. In extreme cases, over pressure can cause injury of workers and property damage. Uncontrolled venting always constitutes an environmental concern.

The present invention also allows any necessary venting of product to the atmosphere to occur after the testing is complete and to be performed in a safe location, typically via a vent or vapor recovery system designed to handle such products. Venting near the point of sampling is not required.

BRIEF DESCRIPTION OF THE DRAWINGS

The preferred embodiment of the invention has been described. Other features, aspects, and advantages of the present invention will become better understood with regard to the following appended claims, and accompanying drawings (which are not to scale) where:

DETAILED DESCRIPTION

Figures 1, 2:
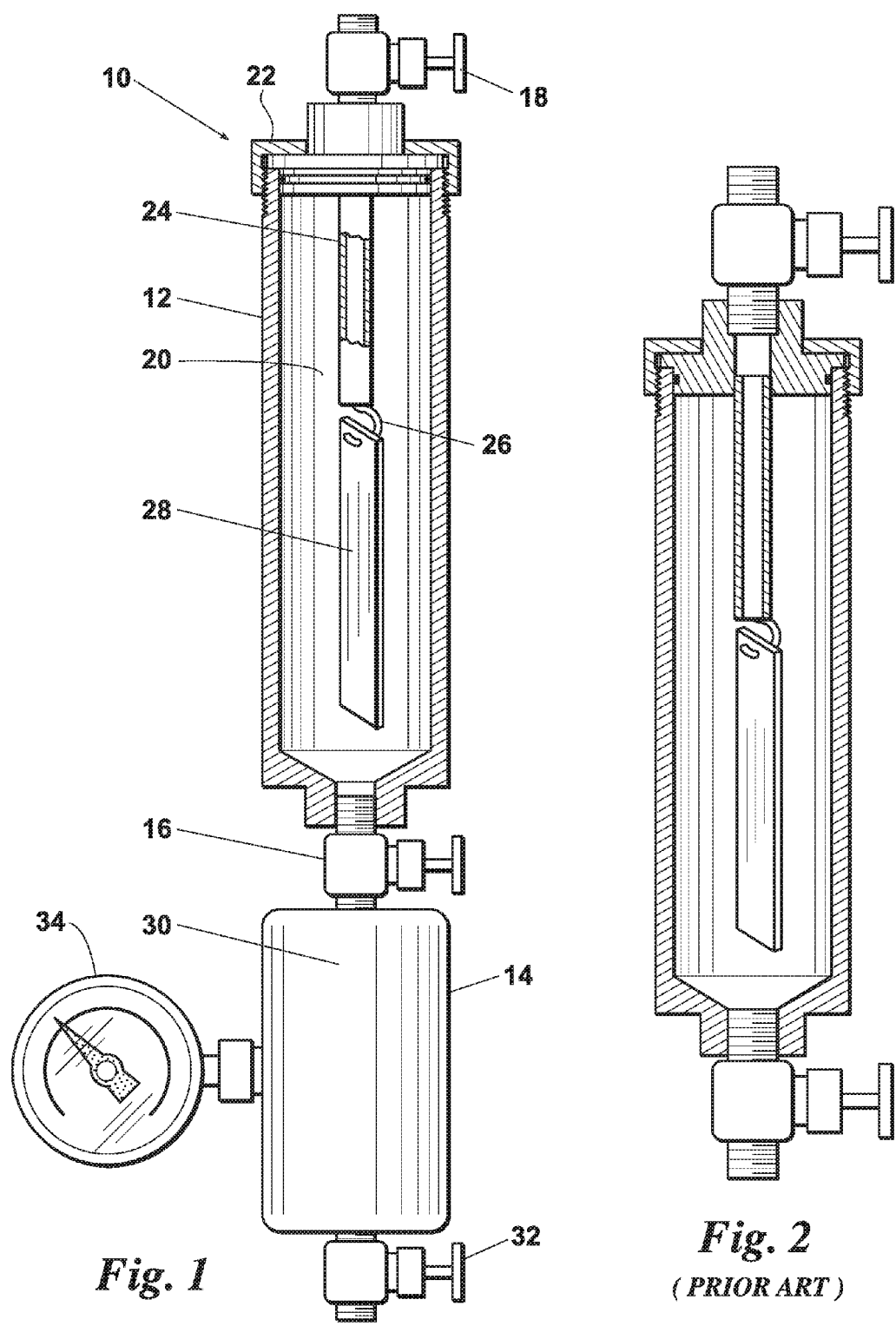
FIG. 1 is a diagram of the preferred embodiment of the present invention.
FIG. 2 is the ASTM specification for the prior art copper strip corrosion test of high vapor pressure hydrocarbon products.

The test apparatus 10 of the present invention uses a first chamber 12 and a second chamber 14 in fluid communication with each other. An isolation valve 16 is located between the first chamber 12 and second chamber 14. The isolation valve 16 is capable of isolating the first chamber 12 from the second chamber 14 or allowing free fluid communication between the first and second chambers 12 and 14. See FIG. 1. In the preferred embodiment the first chamber 12 has an inlet valve 18 for filling the interior 20 of the first chamber 12 with liquid LPG or other high vapor pressure hydrocarbon products. It also contains a means for inserting, hanging and removing copper strips, and a means for cleaning and purging the cylinder.

The preferred embodiment includes a removable cap 22 which threadedly engages with the first chamber 12. When the cap 22 is removed, it provides access to the interior 20 of the first chamber 12 for installing a test strip 28 as well as cleaning and purging the first chamber 12. There is a rod 24 with a hook 26 which extends from the removable cap 22. The hook 26 is sized and located to receive a test strip 28 and to properly suspend the test strip 28 in the liquid phase of the sample in the first chamber 12 after the sample is collected. Further, the inlet valve 18 may be mounted in the removable cap 22.

The second chamber 14 has an empty interior 30 with provisions for cleaning and purging. In the preferred embodiment, there is a purge valve 32 in fluid communication with the second chamber 14, such that it is capable of isolating the second chamber 14 from atmosphere. A second chamber 14 may also be equipped with a pressure gauge 34. The pressure gauge 34 measures and displays the pressure in the second chamber 14.

In the preferred embodiment, the interior 20 of first chamber 12 accounts for approximately 70% of the total volume of the test apparatus 10. The interior 30 of the second chamber 14 provides 30% of the total volume of the test apparatus 10.

The method for testing includes the steps of removing the removable cap 22 from the test apparatus 10. Placing a properly prepared test strip 28 on the hook 26. Placing the rod 24, hook 26 and test strip 28 in the first chamber 12. Installing the removable cap 22 on the test apparatus 10.

When collecting a sample, the completely empty and internally clean apparatus (or containing only a very low pressure residue of a clean inert gas such as helium) will have the inlet valve 18 connected to the sample source using appropriate connecting fittings and hoses or tubing (typically stainless steel). Prior to opening the inlet valve 18, the person collecting the sample must ensure the isolation valve 16 between chamber 12 and chamber 14 is closed and the purge valve 32 is also closed. Once the first chamber 12 is filled with sample, the inlet valve 18 should be closed and the test apparatus 10 must be safely disconnected from the sample source. Note that the purge valve 32 from second chamber 14 should be verified to be in the closed position up to this point and that no leaks are present anywhere in the test apparatus 10. At this point, the first chamber 12 should be full of product and the second chamber 14 is still empty (unless a very low pressure inert gas is intentionally left in the cylinder). The person collecting the product sample can now open the isolation valve 16 to allow some of the sample in the first chamber 12 to flow into and fill the second chamber 14, providing adequate volume for thermal expansion anticipated during the test procedure (with a water bath heating the apparatus to 100 degrees F.). It is important to the test to be sure the test strip 28 is still suspended in the liquid phase of the sample in the first chamber 12 during the one hour test period in the water bath specified in the ASTM test procedure. The pressure gauge 34 in the second chamber 14 will help ensure the sample is allowed to expand into the previously empty second chamber 14 by showing that the second chamber 14 is in fact de-pressured and empty until the product in the liquid-filled first chamber 12 is intentionally allowed to expand into the second chamber 14.

The test method then requires warming the sample and test apparatus 10 to 100 degrees Fahrenheit in a water bath. Maintaining the sample at 100 degrees Fahrenheit for 1 hour. Releasing the sample from the test apparatus 10 by opening the inlet valve 18 or the purge valve 32. In some situations, the sample may be released into the atmosphere. However, in the preferred embodiment, the purge valve 32 will be connected to an exhaust system and the sample is removed in an environmentally friendly and safe manner, typically into a laboratory vent system or a vapor recovery system intended for this type of service. The test strip 28 is then removed from the first chamber 12 and examined for test results using the current ASTM test criteria. The test strip 28 is removed by removing the removable cap 22 from the first chamber 12.

Opening the isolation valve 16 during the process above prevents the possibility of over-pressuring the first chamber 12 due to warming the sample and test apparatus 10 when ambient conditions are warmer than the temperature of the fluid and apparatus. Not only does the addition of the second chamber 14 prevent over-pressuring of the first chamber 12, it also prevents any vapors from escaping to the atmosphere in a hazardous environment where the sample is collected, such as in the process area of a refinery or gas processing plant. The sample and apparatus can be transported safely to a lab and the test run in a safe environment, which is typically provided with a safe and environmentally friendlier system when the apparatus is depressured and opened to examine the test strip 28.

The foregoing description details certain preferred embodiments of the present invention and describes the best mode contemplated. It will be appreciated, however, that changes may be made in the details of construction and the configuration of components without departing from the spirit and scope of the disclosure. Therefore, the description provided herein is to be considered exemplary, rather than limiting, and the true scope of the invention is that defined by the following claims and the full range of equivalency to which each element thereof is entitled.

What is claimed is:

1. A dual chamber test apparatus for copper strip corrosion testing of high vapor pressure products, said test apparatus comprising:
    a first chamber and a second chamber in fluid communication with each other;
    an isolation valve located between the first and second chamber and capable of isolating the first chamber from the second chamber;
    an inlet valve in fluid communication with the first chamber and connectable to a sample supply, wherein the inlet valve is capable of isolating the first chamber;
    a purge valve in fluid communication with the second chamber and capable of isolating the second chamber from atmosphere; and
    a hook located in the first chamber sized to receive a test strip and located so as to properly position the test strip while the corrosion test is being performed.

2. The test apparatus of claim 1 further comprising a pressure gauge on the second chamber, wherein the pressure gauge capable of providing the pressure inside the second chamber.

3. The test apparatus of claim 1 further comprising a removable cap on the first test chamber capable of providing access to an interior portion of the first chamber.

4. The test apparatus of claim 3 further comprising a rod extending from the removable cap and the hook being attached to the rod.

5. A dual chamber test apparatus for copper strip corrosion testing of high vapor pressure products said test apparatus comprising:
    a first chamber and a second chamber in fluid communication with each other;
    an isolation valve located between the first and second chamber and capable of isolating the first chamber from the second chamber;

an inlet valve in fluid communication with the first chamber and connectable to a gas supply, wherein the inlet valve is capable of isolating the first chamber;

a purge valve in fluid communication with the second chamber and capable of isolating the second chamber from atmosphere;

a hook located in the first chamber sized to receive a test strip;

a pressure gauge on the second chamber, wherein the pressure gauge capable of providing the pressure inside the second chamber;

a removable cap on the first chamber capable of providing access to an interior portion of the first chamber; and a rod extending from the removable cap and the hook being attached to the rod.

6. A method for copper strip corrosion testing of high vapor pressure products, the method comprising the steps of:

providing a sample source and a test apparatus having a first chamber, a second chamber, an isolation valve, an inlet valve, a removable cap, a hook, a test strip, a purge valve and a pressure gauge, wherein the first and second chamber are in fluid communication with each other, the isolation valve is located between the first and second chamber, and the inlet valve, removable cap and hook are located in fluid communication with the first chamber and the purge valve is located in fluid communication with the second chamber;

removing the removable cap from the test apparatus;
placing the test strip on the hook;
placing the hook and the test strip in the first chamber of the test apparatus;
installing the removable cap on the test apparatus;
isolating the first chamber from the second chamber by closing the isolation valve;
closing the inlet valve and the purge valve;
attaching the inlet valve to the sample source;
capturing a sample in the first chamber only;
isolating and removing the first chamber from the sample source once the sample is collected in the first chamber;
opening the isolation valve to provide room for thermal expansion of the sample;
warming the sample and test apparatus in a water bath to 100 degrees Fahrenheit;
maintaining the sample at 100 degrees Fahrenheit for 1 hour;
releasing the sample from the test apparatus;
removing the removable cap from the test apparatus;
removing the test strip from the first chamber; and
examining the test strip to determine test results.

7. The method of claim 6, wherein the sample is a high vapor pressure product.

8. The method of claim 7, wherein the sample is selected from the group consisting of LPG, propane, natural gasoline, condensates, and raw natural gas condensates.

9. The method of claim 6 further comprising releasing the sample to atmosphere.

10. The method of claim 6 further comprising:
securing the purge valve to an exhaust system;
opening the purge valve; and
releasing the sample into an exhaust or vapor recovery system.

11. The method of claim 6, wherein capturing the sample comprises opening the inlet valve.

12. The method of claim 6, wherein isolating the first chamber comprises closing the inlet valve.

13. The method of claim 6, wherein warming of the sample is accomplished using a water bath.

* * * * *